US005326559A

United States Patent [19]

Miller

[11] Patent Number: 5,326,559
[45] Date of Patent: Jul. 5, 1994

[54] TREATMENT OF ACCELERATED ATHEOSCLEROSIS WITH INTERLEUKIN-2 RECEPTOR TARGETED MOLECULES

[76] Inventor: D. Douglas Miller, 7295 Greenway Ave., University City, Mo. 63130

[21] Appl. No.: 701,219

[22] Filed: May 16, 1991

[51] Int. Cl.$^5$ .............................................. A61K 37/02
[52] U.S. Cl. .................................. 424/85.2; 435/69.5; 435/69.52; 435/69.7; 435/70.21; 514/824; 514/2; 514/8; 514/21; 935/106; 935/107; 935/109; 424/183.1; 424/144.1
[58] Field of Search ................... 424/85.1, 85.2, 85.8, 424/85.91; 435/69.5, 69.52, 69.7, 70.21; 514/824, 2, 8, 21; 935/106–107, 109

[56] References Cited

FOREIGN PATENT DOCUMENTS 0396387 11/1990 European Pat. Off. .
9101004 1/1991 PCT Int'l Appl. .

OTHER PUBLICATIONS

Clowes et al. Nature 265:625, 1977.
Hoover et al., Cir. Res. 47:578, 1980.
Guyton et al., Cir. Res. 46:625, 1980.
Cunningham et al., Radiology 151:487, 1984.
Shore et al., Cellular Immunol. 100:210, 1986.
Hanson et al., J. Clin. Invest. 81:149, 1988.
Kelley et al., Proc. Nat'l. Acad. Sci, USA 85:3980, 1988.
Schwartz et al., N. Engl. J. Med. 318:1714, 1988.
Heras et al., Circulation 79:657, 1989.
IP et al., J. Am. College Cardiol. 5:1667, 1990.
Lorberboum-Gaski et al., J. Biol. Chem. 265:16311, 1990.
Sarenbock et al., Circulation 82:111-208, 1990.
Muller et al., Circulation 82:111-429, 1990.
Murphy et al., Circulation 82:111-429, 1990.
Casscells et al., Circulation 82:111-208, 1990.
Bastos et al, J. Immunol. 145, 1990, pp. 3535-3539.

Primary Examiner—Garnette D. Draper
Attorney, Agent, or Firm—Fish & Richardson

[57] ABSTRACT

The invention features a method for treating a patient suffering from accelerated atherosclerosis in a patient suffering from vascular damage, e.g., damage caused by percutaneous transluminal coronary angioplasty (PTCA), heart transplantation, or coronary vein graft. The method includes administering to the patient a molecule which is capable of specifically binding to a interleukin receptor expressed on a cell of the patient which contributes to the process of accelerated atherosclerosis. The molecule is capable of decreasing the viability of the cells.

11 Claims, No Drawings

TREATMENT OF ACCELERATED ATHEOSCLEROSIS WITH INTERLEUKIN-2 RECEPTOR TARGETED MOLECULES

BACKGROUND OF THE INVENTION

The field of the invention is inhibition of accelerated atherosclerosis.

Accelerated atherosclerosis is a proliferative process leading to vascular stenosis which commonly occurs following percutaneous transluminal coronary angioplasty (PTCA), heart transplantation, and coronary vein graft. The process is characterized by platelet activation, thrombus formation, and smooth muscle cell hyperproliferation. Accelerated atherosclerosis leads to vascular stenosis in 35–50% of the patients who have undergone PTCA.

Injury of the vascular endothelium is thought to be the initiating event in both spontaneous and accelerated atherosclerosis. Accelerated atherosclerosis commonly occurs following denuding endothelial injury; such injury can be caused by transluminal coronary angioplasty, heart transplantation, and coronary vein graft and is sometimes accompanied by damage to the intima and media. In contrast, spontaneous atherosclerosis is thought to be caused by functional impairment of the endothelium caused by non-denuding, chronic damage of the vascular wall. In both cases, smooth muscle cell hyperproliferation is one of the primary causes of vascular stenosis.

In accelerated atherosclerosis, endothelial damage is followed by accumulation of platelets, monocytes, and lymphocytes; thrombosis; smooth muscle cell migration and proliferation; and lipid accumulation. Interactions between blood borne cells and injured endothelial tissue are thought to create an environment conducive to smooth muscle cell proliferation. Important contributors to this process include, the loss of the inhibitory effect of an intact endothelial layer; release of mitogenic factors by platlets monocytes/macrophages, injured endothelial cells, and smooth muscle cells; activation of T-lymphocytes and monocytes/macrophages; and thrombosis.

Each of the cell types involved in accelerated atherosclerosis may play a role in smooth muscle cell proliferation. Platelets produce platelet-derived growth factor (PDGF), a potent smooth muscle cell mitogen; damaged endothelium, monocytes/macrophages, and smooth muscle cells can all generate a PDGF-like growth factor. Activated monocytes/macrophages, stimulated endothelial cells, and stimulated smooth muscle cells produce interleukin-1, a factor which stimulates proliferation of endothelial cells and smooth muscle cells. Other factors produced by platelets and atheroma cells which are mitogenic for myocytes include: α-fibroblast growth factor, β-fibroblast growth factor, serotonin, and thrombospondin.

Activated T-lymphocytes are present in atherosclerotic plagues and may play a role in several of the processes involved in accelerated atherosclerosis. They release lymphokines and interleukins which can regulate lipoprotein uptake by monocytes/macrophages and which may up-regulate expression of growth factor receptors on smooth muscle cells. Activated T-lymphocytes also release chemotactic factors which enhance migration and adhesion of monocytes/macrophages.

Methods for prevention of accelerated atherosclerosis are generally designed to decrease either thrombogenesis or cell proliferation. Using a baboon vascular graft model, Hanson et al. (*J. Clin. Invest.* 81:149, 1988) demonstrated that anti-glycoprotein IIb/IIIa monoclonal antibodies reduced acute graft closure secondary to thrombosis by 72%. Using the same monoclonal antibody, Bates et al. (*Circulation* 78:II-289, 1988) demonstrated a reduction in coronary thrombosis after coronary angioplasty in dogs. Badimon et al. (*J. Am. Coll. Cardiol.* II Supl. A:30A, 1988) demonstrated an 81% reduction in platelet deposition on de-endothelialized vessel wall in swine treated with a monoclonal antibody directed against von Willebrand factor. Heras et al. (*Circulation* 79:657, 1981) found that recombinant hirudin significantly decreases platelet and fibrinogen deposition in swine subjected to balloon angioplasty. Sarenbock et al. reported similar results following air desiccation injury in rabbits (*Circulation* 82:III-208, 1990). Thrombin inhibitors have been shown to reduce thrombosis following carotid artery endarterectomy in baboons (Schneider et al., *Circulation* 78:II-311, 1988; Jang et al., *Circulation* 78:II-311, 1988). Acetylsalicylic acid pre-treatment has been shown to reduce platelet accumulation in patients who have undergone coronary angioplasty (Cunningham et al., *Radiology* 151:487, 1984). A placebo controlled study in 376 patients demonstrated that while an aspirin-dipyridamole "antiplatelet regimen before and after PTCA did not reduce the six-month rate of restenosis after successful coronary angioplasty, it markedly reduced the incidence of transmural myocardial infarction during or soon after PTCA" (Schwartz et al., *N. Engl. J. Med.* 318:1714, 1988).

Heparin is commonly used following coronary angioplasty to reduce the incidence of acute thrombotic occlusion. Heparin may also have antiproliferative activity, and thus may be useful in prevention of restenosis. Heparin has been shown to reduce platelet accumulation on denuded neointima (Mustard, *Ann. R. Coll. Physicians Surg. Can.* 14:22, 1981). A study found that intravenous heparin in doses large enough to cause continuous anticoagulation reduced myointimal thickening in rats whose carotid arteries had been injured (Clowes et al., *Nature* 265:625, 1977). An in vivo study found that heparin inhibits smooth muscle cell proliferation which occurs after denudation of endothelium by air-drying the rat carotid artery; this effect does not depend on anticoagulant activity (Guyton et al., *Circ. Res.* 46:625, 1980). In vitro studies of cultured rat smooth muscle cells demonstrated that heparin, in either its high anticoagulant form or its non-anticoagulant form, significantly inhibits cell proliferation (Hoover et al., *Circ. Res.* 47:578, 1980). Gordon et al. (*Circulation* 76:IV-213, 1987) demonstrated that arterial smooth muscle cell proliferation following balloon catheter injury in rats was significantly reduced by administration of low molecular weight heparin.

Methotrexate and azathioprine have been investigated as antiproliferative agents for treatment of restenosis (Murphy et al. *Circulation* 82:III-429, 1990; Muller et al. *Circulation* 82:III-429, 1990).

Wai et al. (*Circulation* 82:III-208, 1990) found that a hybrid protein consisting of the ribosome inhibitor, saponin, fused to basic fibroblast growth factor (FGF) killed proliferating, FGF receptor-expressing smooth muscle cells, but not quiescent receptor negative cells;

SUMMARY OF THE INVENTION

In general, the invention features a method for inhibiting accelerated atherosclerosis in a patient suffering from vascular injury, the method includes administering to the patient a molecule which is capable of specifically binding to an interleukin receptor expressed on a cell of the patient which contributes to the process of accelerated atherosclerosis, the molecule being capable of decreasing the viability of the cell.

In preferred embodiments, the cell is a lymphocyte; the cell is a macrophage; the interleukin receptor is an interleukin-2 receptor; the interleukin-2 receptor is a high affinity interleukin-2 receptor; the interleukin receptor is an interleukin-4 receptor; the interleukin receptor is an interleukin-6 receptor; the vascular injury is caused by angioplasty; the vascular injury is caused by coronary vein graft; the vascular injury is caused by cardiac transplant surgery; and the molecule kills cells bearing the interleukin receptor.

In another preferred embodiment, the molecule is a hybrid molecule which includes a first and a second portion joined together covalently, the first portion includes a molecule capable of decreasing cell viability and the second portion includes a molecule capable of specifically binding to the interleukin receptor.

In more preferred embodiments, the second portion includes all or a binding portion of an antibody specific for the interleukin receptor; and the antibody is a complement activating antibody.

In other preferred embodiments, the second portion includes all or a binding portion of a ligand for the interleukin receptor; the ligand is an interleukin; the first portion includes a cytotoxin; the cytotoxin is a fragment of a peptide toxin which is enzymatically active but which does not possess generalized eukaryotic receptor binding activity.

In an even more preferred embodiment, the fragment of a peptide toxin includes fragment A of diphtheria toxin and enough of fragment B of diphtheria toxin to facilitate transport into the cytosol.

In yet more preferred embodiments, the molecule is $DAB_{389}IL-2$; the molecule is $DAB_{389}IL-4$; the molecule is $DAB_{389}IL-6$; the molecule is $DAB_{486}IL-2$; the molecule is $DAB_{486}IL-4$; and the molecule is $DAB_{486}IL-6$.

By "accelerated atherosclerosis" is meant the pathophysiologic response leading to partial or complete stenosis following vascular injury. By "specifically binding" is meant that the molecule does not substantially bind to other cell receptors. By "reduces viability" is meant kills or interferes with proliferation. By "ligand" is meant a molecule which is capable of binding to a protein.

By decreasing the viability of activated cells which bear an interleukin receptor and which play a role in the cascade of proliferative events (e.g., smooth muscle cell proliferation) leading to vascular occlusion following denuding endothelial injury, the method of the invention can effectively inhibit accelerated atherosclerosis and vascular occlusion.

Other features and advantages of the invention will be apparent from the following description of the preferred embodiments thereof, and from the claims.

DETAILED DESCRIPTION

Decreasing the viability of activated monocytes/macrophages and lymphocytes provides a means for decreasing the production of lymphokines and mitogens which are important contributors to accelerated atherosclerosis. Activated monocytes/macrophages and activated T-lymphocytes express the high affinity interleukin-2 receptor (IL-2R); since this receptor is not expressed on resting cells, it provides a means by which to target activated immune cells while not interfering with resting cells. Molecules designed to recognize the high affinity IL-2R will recognize activated monocytes/macrophages and activated T-lymphocytes and can be used to selectively decrease the viability of such cells. In addition, activated lymphocytes and monocytes/macrophages can express receptors for other interleukins such as interleukin-4 and interleukin-6. These receptors, like the interleukin-2 receptor, provide a means by which to target activated cells which contribute to accelerated atherosclerosis.

Molecules Useful in the Method of the Invention

In general, there are three ways in which the molecules useful in the invention can act: (1) the molecule can kill a cell because the molecule has a cytotoxic domain; (2) the molecule (an antibody) can cause cell lysis by inducing complement fixation; and (3) the molecule can block binding or uptake of receptor's ligand. In all three cases the molecule must be targeted to receptor bearing cells this is accomplished by including the receptor's ligand (or a portion or derivative thereof) or an anti-receptor antibody as part of the molecule.

Interleukin-2 receptor (IL-2R) targeted molecules useful for treatment of accelerated atherosclerosis provide examples of each of these three approaches. A fusion molecule which includes the IL-2R binding portion of interleukin-2 (IL-2) and a cytotoxin can be used to kill activated lymphocytes and monocytes/macrophages associated with inflammatory arthritis. Likewise, the second type of molecule described above, a complement fixing antibody, in this instance directed against the IL-2 receptor, can eliminate IL-2 receptor-bearing cells. In this example, the third type of molecule could be a molecule that blocks binding of IL-2 to its receptor. This molecule would prevent infected cells from receiving a proliferation signal from IL-2 nd thus could suppress the inflammatory response.

Molecules useful for treating patients with inflammatory arthritis can take a number of forms. When IL-2 itself is the targeting agent, the molecule can be a cytotoxic hybrid molecule in which IL-2 is fused to a toxin molecule, preferably a polypeptide toxin. Derivatives of IL-2 which bind to IL-2R, lack IL-2 activity and block binding and/or uptake of bona fide IL-2 are useful in the method of the invention because they will prevent IL-2-induced proliferation of IL-2R bearing cells. When an anti-IL-2R antibody is the targeting agent, a cytotoxic hybrid molecule can be formed by fusing all or part of the antibody to a cytotoxin. The effectiveness of such an antibody/toxin hybrid, like that of an IL-2/toxin hybrid, depends on the hybrid molecule being taken up by cells to which it binds. Anti-IL-2R antibodies which block binding and/or uptake of IL-2 are also useful in the method of the invention. Lytic anti-IL-2R antibodies are useful in the invention because they can cause complement-mediated lysis of IL-2R-bearing cells.

Some of the molecules can be hybrid molecules formed by the fusion of all or part of two or more molecules. The hybrid molecule can be a hybrid protein encoded by a recombinant DNA molecule, in which case the two domains are joined (directly or through an intermediary domain) by a peptide bond. Alternatively, two domains can be produced separately and joined by a covalent bond in a separate chemical linkage step. In some cases, the cytotoxic domain of a hybrid molecule may itself be derived from two separate molecules.

Interleukin-2 as a Targeting Agent

Interleukin-2 (IL-2) or any IL-2 receptor binding derivative thereof can be used as a targeting agent for a cytotoxin. The DNA and amino acid sequences of IL-2 are known (Tadatsugu et al., *Nature* 302:305, 1983), and its structure has been predicted by x-ray crystallography (Brandhuber et al., *Science* 238:1707, 1987). Analysis of genetically engineered variants of IL-2 has provided some information concerning which residues are important for IL-2R binding (Collins et al., *Proc. Natl. Acad. Sci. USA* 85:7709, 1988) and bioactivity (Cohen et al. *Science* 234:349, 1989; Collins et al., supra). Variants of IL-2 which are useful in the invention include deletion mutants (Genbauffe et al., U.S. Ser No. 388,557, hereby incorporated by reference) which lack one or more amino acid residues in the region between residue 74 and residue 79 (numbering according to Williams et al., *Nucl. Acids Res.* 16:1045, 1988). These mutants effectively target toxins to IL-2R-bearing cells (Genbauffe et al., supra). Generally, IL-2 variants useful for targeting a cytotoxin must efficiently bind IL-2R and be endocytosed. The ability of various derivatives to bind to the IL-2 receptor can be tested with an IL-2R binding assay described below.

In designing molecules targeted to cells bearing the IL-2 receptor it must be recognized that the IL-2 receptor, like other receptors, has several forms; and it may be desirable to target cells bearing one form and not another. The human interleukin-2 receptor has a high-, an intermediate-, and a low-affinity form. The high affinity receptor has an apparent $K_d$ of $\sim 10^{-10}$M and is composed of two subunits, p55 and p75 (also called p70). When expressed on the cell surface, both the p75 and p55 subunits are capable of binding IL-2. The p75 subunit corresponds to the intermediate affinity receptor ($K_d \sim 8.2 \times 10^{-10}$M), and p55 subunit corresponds to the low affinity receptor ($K_d \sim 1-3 \times 10^{-8}$M). The p75 subunit is expressed on the surface of resting T cells, natural killer cells, monocytes/macrophages, and lymphokine-activated killer (LAK) cell precursors, while the high affinity receptor is expressed on activated T- and B-cells.

In the method of the invention it may be desirable to target only cells bearing the high affinity receptor. In these circumstances useful molecules will eliminate or neutralize cells bearing the high affinity IL-2 receptor at a concentration which leaves cells bearing the intermediate or low affinity receptor largely unaffected. When the molecule, like IL-2 itself, has affinity for all three classes of IL-2 receptor, selectivity can be accomplished by administering the molecule at a concentration which does not permit significant binding to cells bearing lower affinity receptors. A hybrid molecule may have altered receptor affinities compared to IL-2. Such hybrid molecules may be more or less selective for cells bearing the high affinity IL-2 receptor. For example, cells bearing the high-affinity receptor are 500–1000 times more sensitive to $DAB_{486}IL$-2, a fusion protein consisting of part of diphtheria toxin and part of IL-2, than are cells bearing the intermediate-affinity receptor (Waters et al., *Eur. J. Immunol.* 20:785, 1990).

A cytotoxin can be attached to an IL-2 derivative in a number of ways. Preferably, an IL-2/toxin hybrid is a hybrid protein produced by the expression of a fused gene. Alternatively, the cytotoxin and the IL-2 derivative can be produced separately and later coupled by means of a non-peptide covalent bond. Linkage methods are described below.

Useful cytotoxins are preferably significantly cytotoxic only when present intracellularly and are substantially excluded from any given cell in the absence of a targeting domain. Peptide toxins fulfill both of these criteria and are readily incorporated into hybrid molecules. A mixed cytotoxin, a cytotoxin composed of all or part of two or more toxins, can also be used. Several useful toxins are described in more detail below.

Interleukin-4 and Interleukin-6 as a Targeting Agents

Interleukin-4 (IL-4) is a cytokine which acts on a variety of cell types. Its receptor is expressed on a number of cell types, including CD4+T cells and monocytes. IL-4 can act as a T-lymphocyte cell growth factor and it is thought to have an influence on IL-2 induced lymphocyte proliferation.

A cytotoxin directed against IL-4 receptor-bearing cells or IL-6 receptor-bearing cells may enhance the effectiveness of molecules directed against IL-2R-bearing cells. The protein and DNA sequence of IL-4 and IL-6 are known (Lee et al., *J. Biol. Chem.* 263:10817, 1988; Hirano et al., Nature 324:73, 1986). These lymphokines can be used to create hybrid lymphokine/toxin molecules similar to IL-2/toxin hybrid molecules.

Monoclonal Antibodies as Targeting Agents

Monoclonal antibodies directed against the lymphokine receptor of choice can be used to direct toxins to cells bearing that receptor. These antibodies or antibody fragments can be fused to a cytotoxin either by virtue of the toxin and the antibody being encoded by a fused gene which encodes a hybrid protein molecule, or by means of a non-peptide covalent bond which is used to join separately produced ligand and toxin molecules. Several useful toxins are described below.

Antibody/toxin hybrids can be tested for their ability to kill receptor bearing cells using a toxicity assay similar to that which is described below for IL-2R bearing cells.

Monoclonal antibodies useful in the method of the invention can be made by immunizing mice with human IL-2R or cultured T-lymphocytes, fusing the murine splenocytes with appropriate myeloma cells, and screening the antibodies produced by the resultant hybridoma lines for the requisite IL-2R binding properties by means of an ELISA assay. Antibody production and screening can be performed according to Uchiyama et al. (*J. Immunol.* 126:1393, 1981). Alternatively, useful antibodies may be isolated from a combinatorial library produced by the method of Huse et al. (*Science* 246:1275, 1989).

The invention can employ not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778); or a chimeric antibody, for example, a "humanized" antibody which contains the binding specificity of a murine antibody, but in which most or all of the remaining portions are of human origin (Reichman et al., *Nature* 332:323, 1988).

Toxins

The toxin molecules useful in the method of the invention are preferably toxins, such as peptide toxins, which are significantly cytotoxic only when present intracellularly. Of course, under these circumstances the molecule must be able to enter a cell bearing the targeted receptor. This ability depends on the nature of the molecule and the nature of the cell receptor. For example cell receptors which naturally allow uptake of a ligand are likely to provide a means for a molecule which includes a toxin to enter a cell bearing that receptor. Preferably, a peptide toxin is fused to an IL-2R binding domain by producing a recombinant DNA molecule which encodes a hybrid protein molecule. Such an approach ensures consistency of composition.

Many peptide toxins have a generalized eukaryotic receptor binding domain; in these instances the toxin must be modified to prevent generalized intoxication of non-receptor bearing cells. Any such modifications must be made in a manner which preserves the cytotoxic functions of the molecule (see U.S. Department of Health and Human Services, U.S. Ser. No. 401,412). Potentially useful toxins include, but are not limited to: cholera toxin, ricin, 0-Shiga-like toxin (SLT-I, SLT-II, SLT II$_V$), LT toxin, C3 toxin, Shiga toxin, pertussis toxin, tetanus toxin, *Pseudomonas* exotoxin, alorin, saporin, modeccin, and gelanin.

Diphtheria Toxin-based Molecules

Diphtheria toxin can be used to produce molecules useful in the method of the invention. Diphtheria toxin, whose sequence is known, is described in detail in Murphy U.S. Pat. No. 4,675,382, hereby incorporated by reference. The natural diphtheria toxin molecule secreted by *Corynebacterium diphtheriae* consists of several functional domains which can be characterized, starting at the amino terminal end of the molecule, as enzymatically-active Fragment A (amino acids $Gly_1$ - $Arg_{193}$) and Fragment B (amino acids $Ser_{194}$ - $Ser_{535}$), which includes a translocation domain and a generalized cell binding domain (amino acid residues 475 through 535).

The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage between fragments A and B; (iv) as the pH of the endocytic vesicle decreases to below 6, the toxin crosses the endosomal membrane, facilitating the delivery of Fragment A into the cytosol; (v) the catalytic activity of Fragment A (i.e., the nicotinamide adenine dinucleotide—dependent adenosine diphosphate(ADP) ribosylation of the eukaryotic protein synthesis factor termed "Elongation Factor 2") causes the death of the intoxicated cell. It is apparent that a single molecule of Fragment A introduced into the cytosol is sufficient to block down the cell's protein synthesis machinery and kill the cell. The mechanism of cell killing by *Pseudomonas* exotoxin A, and possibly by certain other naturally-occurring toxins, is very similar.

$DAB_{486}IL$-2, a fusion protein in which the receptor binding domain of diphtheria toxin has been replaced by a portion of human IL-2 (Williams et al., *J. Biol. Chem.* 35:20673, 1990; see also Williams et al., *Protein Eng.* 1:493, 1987), is an example of a molecule useful in the method of the invention. This molecule selectively kills IL-2R-expressing tumor cells and lymphocytes (Waters et al., *Eur. J. Immunol.* 20:785, 1990; Kiyokawa et al., *Cancer Res.* 49:4042, 1989). Because of its ability to kill activated lymphocytes, $DAB_{486}IL$-2 has been used to control graft rejection (Pankewycz et al., *Transplantation* 47:3187, 1989; Kickman et al., *Transplantation* 47:327, 1989) and to treat certain autoimmune disorders (Forte et al., 2nd *International Symposium on Immunotoxins*, 1990).

$DAB_{486}IL$-2 is a chimeric molecule consisting of Met followed by amino acid residues 1 through 485 of the mature diphtheria toxin fused to amino acid residues 2 through 133 of IL-2. Thus, $DAB_{486}IL$-2 includes all of diphtheria toxin fragment A, which encodes the enzymatically active portion of the molecule, and a portion of fragment B. The portion of fragment B present in $DAB_{486}IL$-2 does not include the generalized receptor binding domain but does include the translocation domain which facilitates delivery of the enzymatically active portion into the cytosol.

Preparation of $DAB_{486}IL$-2 and $DAB_{389}IL$-2

$DAB_{486}IL$-2 was produced in *E. coli* harboring the $DAB_{486}IL$-2 encoding plasmid, pDW24 (Williams et al., *J. Biol. Chem.* 265:20673, 1990, except $amp^r$ is replaced by $kan^r$). The protein was purified by immunoaffinity chromatography and high pressure liquid chromatography (Williams et al., supra). $DAB_{389}IL$-2 can be prepared as described below for $DAB_{389}IL$-4 by substituting IL-2 for IL-4.

Preparation of $DAB_{389}IL$-4 and $DAB_{486}IL$-2

A synthetic gene encoding human interleukin-4 was synthesized (Milligen/Biosearch 7500 DNA synthesizer). The IL-4 sequence (Yodota et al., *Proc Nat'l Acad Sci. USA*, 83:58994, 1986) was modified to incorporate *E. coli*-preferred codon usage (deBoer et al., in *Maximizing Gene Expression*, Reznikioff et al., eds. 1986, Butterworths, Boston), and restriction endonuclease cleavage sites were added to facilitate subsequent cloning steps. IL-4 coding sequence ($His^1$ to $Ser^{129}$) was inserted into pDW27 plasmid. pDW27 is derived from pDW24 (Williams et al., *J. Biol. Chem.* 265:11885, 1990) by deleting DNA corresponding to amino acids 388 to 485 of native diphtheria toxin. $DAB_{486}IL$-4 can be prepared as described above for $DAB_{486}IL$-2 by substituting IL-4 for IL-2.

Cytotoxicity of $DAB_{389}IL$-4

The ability of $DAB_{389}IL$-4 to reduce viability of various cell types was measured using an inhibition of protein synthesis assay; the results of this assay are presented $IC_{50}$ concentration 89IL-4 required for a 50% decrease in protein synthesis. The rat, Con A-activated, normal splenic lymphocytes were far less sensitive to $DAB_{389}IL$-4 than any of the other cells or cell lines. Since the rat interleukin-4 receptor does not bind human interleukin-4, this result demonstrates the specificity of $DAB_{389}IL$-4. These rat cells are sensitive to a diphtheria toxin/rat interleukin-2 hybrid molecule.

TABLE 1

DAB$_{389}$IL-4 Sensitivity of Normal and Neoplastic Cells and Cell Lines

| Cell or Cell Line | Classification | IC$_{50}$ (M) |
| --- | --- | --- |
| T cell origin | | |
| HUT 102/6TG | Human, CTCL, HTLV-I+ | $2.9 \times 10^{-11}$ |
| C91/PL | Human, HTLV-I+, transformed | $6.3 \times 10^{-11}$ |
| B cell origin | | |
| Raji | Human, Burkitt's lymphoma EBV+ | $7.2 \times 10^{-10}$ |
| Myelomononuclear cell | | |
| U937 | Human, histiocytic lymphoma | $2.0 \times 10^{-9}$ |
| Normal PBMC | | |
| PHA activated T cells | Human | $1.6 \times 10^{-10}$ |
| Non-primate | | |
| con A-activated normal splenic T cells | Rat | $>10^{-7}$ |

Preparation of DAB$_{389}$IL-6 and DAB$_{486}$IL-6

A synthetic gene encoding human interleukin-6 was synthesized (Milligen/Biosearch 7500 DNA synthesizer). The IL-6 sequence (Revel et al., EPA 8611404.9) was modified to incorporate E. Coli preferred codon usage (deBoer et al., supra), and restriction endonuclease cleavage sites were added to facilitate subsequent cloning steps. The entire IL-6 coding sequence was inserted into pDW27 plasmid as described above for DAB$_{389}$IL-4. DAB$_{486}$IL-6 can be produced as described above for DAB$_{486}$IL-2 by substituting IL-6 for IL-2.

Mixed Toxins

The cytotoxic portion of some molecules useful in the invention can be provided by a mixed toxin molecule. A mixed toxin molecule is a molecule derived from two different polypeptide toxins. Generally, as discussed above in connection with diphtheria toxin, polypeptide toxins have, in addition to the domain responsible for generalized eukaryotic cell binding, an enzymatically active domain and a translocation domain. The binding and translocation domains are required for cell recognition and toxin entry respectively. The enzymatically active domain is the domain responsible for cytotoxic activity once the molecule is inside a cell.

Naturally-occurring proteins which are known to have a translocation domain include diphtheria toxin, Pseudomonas exotoxin A, and possibly other peptide toxins. The translocation domains of diphtheria toxin and Pseudomonas exotoxin A are well characterized (see, e.g., Hoch et al., *Proc. Natl. Acad. Sci. USA* 82:1692, 1985; Colombatti et al., *J. Biol. Chem.* 261:3030, 1986; and Deleers, et al., *FEBS Lett.* 160:82, 1983), and the existence and location of such a domain in other molecules may be determined by methods such as those employed by Hwang et al., *Cell* 48:129, 1987; and Gray et al., *Proc. Natl. Acad. Sci. USA* 81:2645, 1984).

One useful IL-2/mixed toxin hybrid molecule is formed by fusing the enzymatically active A subunit of E. coli Shiga-like toxin (Calderwood et al., *Proc. Natl. Acad. Sci. USA* 84:4364, 1987) to the translocation domain (amino acid residues 202 through 460) of diphtheria toxin, and to IL-2. This three-part hybrid molecule, SLT-A/DTB'/IL-2, is useful in the method of the invention in the same way as DAB$_{486}$IL-2 described above. The IL-2 portion of the three-part hybrid causes the molecule to attach specifically to IL-2R-bearing cells, and the diphtheria toxin translocation portion assists in the insertion of the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell. The difference between these two types of hybrid toxins is the nature of their enzymatic activities: the enzymatic portion of DAB$_{485}$IL-2 catalyzes the ADP-ribosylation by nicotinamide adenine dinucleotide of Elongation Factor 2, thereby inactivating this factor which is necessary for protein synthesis, while the enzymatic portion of SLT-A/DTB'/IL-2 is a ribonuclease capable of cleaving ribosomal RNA at a critical site, thereby inactivating the ribosome. SLT-A/DTB'/IL-2 hybrid would therefore be useful as a treatment for the same indications as DAB$_{486}$IL-2, and could be substituted or used in conjunction with it.

Linkage of Toxins to Binding Ligands

The binding ligand and the cytotoxin of useful hybrid molecules can be linked in several ways. If the hybrid molecule is produced by expression of a fused gene, a peptide bond serves as the link between the cytotoxin and the binding ligand. Alternatively, the toxin and the binding ligand can be produced separately and later coupled by means of a non-peptide covalent bond.

For example, the covalent linkage may take the form of a disulfide bond. In this case, if the IL-2R binding ligand is a protein, e.g., IL-2, the DNA encoding IL-2 can be engineered to contain an extra cysteine codon as described in Murphy et al. U.S. Ser. No. 313,599, now U.S. Pat. No. 5,080,898, hereby incorporated by reference. The cysteine must be positioned so as to not interfere with the IL-2R binding activity of the molecule. For example, the cysteine codon can be inserted just upstream of the DNA encoding Pro$^2$ of the mature form of IL-2. The toxin molecule must be derivatized with a sulfhydryl group reactive with the cysteine the modified IL-2. In the case of a peptide toxin this can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described in Hiskey (*Peptides* 3:137, 1981). Derivatization can also be carried out according to the method described for the derivatization of a peptide hormone in Bacha et al. U.S. Pat. No. 4,468,382, hereby incorporated by reference. Similarly, proteins can be derivatized at the DNA or protein chemistry level. The introduction of sulfhydryl groups into proteins is described in Maasen et al. (*Eur. J. Biochem.* 134:32, 1983). The cytotoxin and the IL-2R binding ligand are then produced and purified, and the disulfide bond between the purified molecules formed by reducing both sulfur groups, mixing toxin and ligand, in a ratio of about 1:5 to 1:20, and allowing disulfide bond formation to proceed to completion (generally 20 to 30 minutes) at room temperature. The mixture is then dialyzed against phosphate buffered saline to remove unreacted ligand and toxin molecules. Sephadex chromatography or the like is then carried out to separate on the basis of size the desired toxin-ligand conjugates from toxin-toxin and ligand-ligand conjugates.

Assays for IL-2 Receptor Binding and IL-4 Receptor Binding

The IL-2R binding ability of various molecules can be measured using an IL-2R assay for high affinity (Ju et al., *J. Biol. Chem.* 262:5723, 1987) or intermediate affinity receptors (Rob et al., *Proc. Natl. Acad. Sci. USA* 84:2002, 1987). The IL-4R binding activity of various molecules can be measured using the assay described by Park et al. (*J. Exp. Med.* 66:176, 1984) or the assay described by Foxwell et al. (*Eur. J. Immunol.* 19:1637, 1989).

Assays for Toxicity

Molecules of the invention (both antibodies and hybrid molecules) can be screened for the ability to decrease viability of cells bearing the targeted receptor by means of assays such as those described below.

Toxicity towards IL-2R bearing cells can be tested as follows. Cultured HUT 102/6TG (Tsudo et al., *Proc. Natl. Acad. Sci. USA* 83:9694, 1986) or YT2C2 (Teshigiwari et al., *J Exp. Med.* 165:223, 1987 cells are maintained in RPMI 1640 medium (Gibco, Grand Island, N.Y.) supplemented with 25 mM HEPES (pH 7.4), 2 mM 1-glutamine, 100 U/ml penicillin, 100 μg/ml streptomycin, and 10% fetal calf serum (Hazelton, Lenexa, Kans.). Cells are seeded in 96-well V-bottomed plates (Linbro-Flow Laboratories, McLean, Va.) at a concentration of $1 \times 10^5$ per well in complete medium. Putative toxins are added to varying concentrations ($10^{-12}M$ to $10^{-6}M$) and the cultures are incubated for 18 hrs. at 37° C. in a 5% $CO_2$ atmosphere. Following incubation, the plates are centrifuged for 5 min. at $170 \times g$, and the medium removed and replaced with 100 μl leucine-free medium (MEM, Gibco) containing 8 μCi/ml ($^3$H-leucine; New England Nuclear, Boston, Mass.). After an additional 90 min. at 37° C., the plates are centrifuged for 5 min. at $170 \times g$, the medium is removed, and the cells are collected on glass fiber filters using a cell harvester (Skatron, Sterling, Va.). Filters are washed, dried, and counted according to standard methods. Cells cultured with medium alone serve as the control.

Toxicity towards cells bearing IL-4R may be tested by an assay similar to that described above for IL-2R bearing cells, but utilizing MLA144 cells (Rabin et al. *J. Immunol.* 127:1852, 1981) or HUT 102/6TG cells, seeded at $1 \times 10^5$ cells per well and incubated for 40 hours.

DAB$_{486}$IL-2 Prevents Restenosis in an Animal Model

Aortic angioplasty (4 atmospheres $\times$ 30 s $\times$ 2) was performed on 17 atherogenic rabbits. Eleven of the rabbits were treated with DAB$_{486}$IL-2 (0.1 mg/kg/day, intravenously) for 10 days post-angioplasty and 6 were treated with a placebo. Aortic angioplasty and non-angioplasty sites were studied by quantitative angiography at baseline (immediately post-angioplasty) and 6 weeks post-angioplasty. Quantitative histomorphometry of angioplasty sites was performed 6 weeks post angioplasty to measure intimal thickness. Referring to Table 2, DAB$_{486}$IL-2, treatment with DAB$_{486}$IL-2 essentially eliminated post-angioplasty restenosis.

TABLE 2

| | Effect of DAB$_{486}$IL-2 on Post-Angioplasty Restenosis | | |
|---|---|---|---|
| | % Change in Luminal Diameter | | Intimal Thickness- |
| | Angioplasty Site | Non-Angioplasty Site | Angioplasty Site |
| Placebo | 18 ± 9 | 3 ± 3 | 354 ± 92 μ |
| DAB$_{486}$IL-2 | −1 ± 5 | −1 ± 7 | 159 ± 111 μ |

Therapy

Generally, the molecules of the invention will be administered by intravenous infusion. They may also be administered subcutaneously. Dosages of molecules useful in the methods of the invention will vary, depending on factors such as whether the substance is a cytotoxin, a lytic antibody, or an IL-2R blocking molecule. In the case of toxic molecules that act intracellularly, the extent of cell uptake is an important factor; less permeable molecules must be administered at a higher dose.

More than 60 patients have received DAB$_{486}$IL-2 in Phase I/II clinical protocols. The maximum tolerated dose (MTD) established by transient asymptomatic hepatic transaminase elevations in about 30% of patients treated at the MTD. Serum concentrations of $10^{-8}M$ DAB$_{486}$IL-2 have been achieved in patients with IL-2 receptor expressing malignancies. Animal and human studies have demonstrated that DAB$_{486}$IL-2 has no general immunosuppressive effect (LeMaistre et al., supra; Woodworth et al., supra).

Experiments indicate that binding and internalization of DAB$_{486}$IL-2 by cells bearing the high affinity IL-2 receptor occurs within 30 minutes of exposure, resulting in maximal inhibition of protein synthesis within several hours. Therefore, the molecule should be effective even if the serum half-life is rather short.

Generally, drugs targeted to IL-2 receptor will be administered immediately after (e.g., within several minutes or less) vascular injury. Preferably, treatment begins before the accumulation of platelets and leukocytes. Animal models of denuding balloon catheter injury have been used to show that platelet aggregation and thrombus formation occurs immediately after injury and that leukocyte adhesion begins within several hours. Autopsy of a patient who died 5 days after angioplasty revealed that proliferating smooth muscle cells were invading the dilated region (Austin et al., *J. Amer. Coll. Cardiol.* 6:369, 1985).

Once initiated, endothelial regeneration is complete within one to two weeks. Since re-endothelialization of the vessel wall appears to inhibit smooth muscle cell proliferation (Ip et al., *J. Amer. Coll. Cardiol.* 15:1667, 1990), treatment may need to last for only a few weeks. Accordingly, it is desirable to administer the compounds of the invention periodically over a period adequate to allow regeneration of the endothelium.

The hybrid molecule can be administered as an unmodified molecule or in the form of a pharmaceutically acceptable salt, admixed with a therapeutically acceptable carrier, e.g., saline. Examples of preferred salts are therapeutically acceptable organic acids, e.g., acetic, lactic, maleic, citric, or salicylic. For example, the hybrid molecule may be purified and sterile filtered using 2 micron filters and suspended in sterile phosphated buffer saline (0.15M NaCl; 0.02M phosphate buffer, pH 7.2).

Other Embodiments

Derivatives of IL-2 which block utilization of endogenous IL-2 are useful for preventing proliferation of IL-2R bearing cells. Activated cells deprived of IL-2 fail to proliferate and, in the absence of the essential anabolic stimulus provided by IL-2, will eventually die. The ability of a given IL-2 derivative to interfere with IL-2 function can be tested in an IL-2 bioactivity assay such as the one described by Ju et al. (*J. Biol. Chem.* 262:5723, 1987). IL-2R/toxin hybrids in which the toxin has been rendered inactive can be also used to block IL-2 receptors. A non-toxic mutant diphtheria toxin molecule has been described (Uchida et al. *J. Biol. Chem.* 248:3838, 1973), and this molecule can be used to produce a non-toxic IL-2/diphtheria toxin hybrid. See Svrluga et al. U.S. Ser. No. 590,113, hereby incorporated by reference, for an example of such a hybrid molecule.

Monoclonal antibodies which interfere with the binding and/or uptake of IL-2 are useful in the method of the invention because IL-2R bearing cells deprived of IL-2 fail to proliferate. Blocking monoclonal antibodies can be tested for their ability to interfere with IL-2 bioactivity using the method of Ju et al., (supra).

Monoclonal antibodies which induce complement can be used to destroy IL-2R-bearing cells. Complement inducing antibodies are generally those of the IgG1, IgG2, IgG3,and IgM isotypes. Monoclonal anti-IL-2R antibodies can be screened for those able to induce complement using a complement-dependent cytotoxicity test, as follows.

Human T-lymphocytes and EBV transformed B-lymphocytes are labeled with $^{51}Cr$ sodium chromate and used as target cells; these cells are incubated with hybridoma culture supernatants and with complement, and then the supernatants are collected and counted with a gamma counter. Those supernatants exhibiting toxicity against activated T-lymphocytes, but not resting T- or B-lymphocytes, are selected, and then subjected to a further screening step to select those supernatants containing antibody which precipitates (i.e., is specifically reactive with) the 50 kd glycoprotein IL-2 receptor (described in detail in Leonard et al. *Proc. Natl. Acad. Sci. USA* 80:6957, 1983). The desired anti-IL-2 receptor antibody is purified from the supernatants using conventional methods.

What is claimed is:

1. A method for inhibiting accelerated atherosclerosis in a patient suffering from vascular injury, said method comprising administering to said patient a molecule which is capable of specifically binding to an interleukin-2 receptor expressed on a cell of said patient which contributes to the process of accelerated atherosclerosis, said molecule being capable of decreasing the viability of said cell, said molecule being a hybrid molecule comprising a first and a second portion joined together covalently, said first portion comprising a cytotoxin capable of decreasing cell viability and said second portion comprising interleukin-2 or an antibody capable of binding to the interleukin-2 receptor.

2. The method of claim 1 wherein said cell is a lymphocyte.

3. The method of claim 1 wherein said interleukin-2 receptor is a high affinity interleukin-2 receptor.

4. The method of claim 1 wherein said vascular injury is caused by angioplasty.

5. The method of claim 1 wherein said vascular injury is caused by coronary vein graft.

6. The method of claim 1 wherein said vascular injury is caused by cardiac transplant surgery.

7. The method of claim 1 wherein said molecule kills cells bearing said interleukin-2 receptor.

8. The method of claim 1 wherein said cytotoxin is a fragment of a peptide toxin which is enzymatically active but which does not possess generalized eukaryotic receptor binding activity.

9. The method of claim 8 wherein said fragment of a peptide toxin comprises fragment A of diphtheria toxin and enough of fragment B of diphtheria toxin to facilitate translocation into the cytosol.

10. The method of claim 9 wherein said molecule is $DAB_{389}IL$-2.

11. The method of claim 9 wherein said molecule is $DAB_{486}IL$-2.

* * * * *

UNITED STATES PATENT AND TRADEMARK OFFICE
CERTIFICATE OF CORRECTION

PATENT NO.   : 5,326,559

DATED        : July 5, 1994

INVENTOR(S)  : D. Douglas Miller

It is certified that error appears in the above-identified patent and that said Letters Patent is hereby corrected as shown below:

On the title page, item (54), and col. 1 line 2, replace "ATHEOSCLEROSIS" with --ATHEROSLEROSIS--;

Column 1, line 41, replace "platlets" with --platelets--;

Column 2, line 15, replace "1981" with --1989--;

Column 8, lines 62-63, correct the lines to read as follows: "presented in Table 1. $IC_{50}$ (M) is the concentration of $DAB_{389}IL-4$...".

Signed and Sealed this

Twentieth Day of September, 1994

Attest:

BRUCE LEHMAN

Attesting Officer   Commissioner of Patents and Trademarks